United States Patent
Cohen (10) Patent No.: US 9,820,695 B2
(45) Date of Patent: Nov. 21, 2017

(54) METHOD FOR DETECTING CONTACT WITH THE WALL OF A REGION OF INTEREST

(75) Inventor: Amit Cohen, Binyamina (IL)

(73) Assignee: St. Jude Medical International Holding S.àr.l., Luxembourg (LU)

( * ) Notice: Subject to any disclaimer, the term of this patent is extended or adjusted under 35 U.S.C. 154(b) by 1215 days.

(21) Appl. No.: 12/748,894

(22) Filed: Mar. 29, 2010

(65) Prior Publication Data
US 2011/0237933 A1 Sep. 29, 2011

(51) Int. Cl.
*A61B 5/00* (2006.01)
*A61B 5/06* (2006.01)

(52) U.S. Cl.
CPC .......... *A61B 5/6885* (2013.01); *A61B 5/062* (2013.01)

(58) Field of Classification Search
CPC .... A61B 2019/5251; A61B 2019/5458; A61B 2562/0209; A61B 5/0422; A61B 5/062; A61B 5/6885; A61N 1/368; A61N 1/3686; A61N 2001/0585; A61N 5/0601
USPC .................................. 600/424, 437; 49/425
See application file for complete search history.

(56) References Cited

U.S. PATENT DOCUMENTS

| | | | |
|---|---|---|---|
| 6,129,669 A | 10/2000 | Panescu et al. | |
| 6,233,476 B1 | 5/2001 | Strommer et al. | |
| 6,266,552 B1 * | 7/2001 | Slettenmark | 600/424 |
| 6,493,575 B1 * | 12/2002 | Kesten et al. | 600/431 |
| 6,726,651 B1 * | 4/2004 | Robinson et al. | 604/101.01 |
| 7,197,354 B2 | 3/2007 | Sobe | |
| 7,343,195 B2 | 3/2008 | Strommer et al. | |
| 7,386,339 B2 | 6/2008 | Strommer et al. | |
| 7,397,935 B2 | 7/2008 | Kimmel et al. | |
| 7,505,809 B2 | 3/2009 | Strommer et al. | |
| 2004/0249281 A1 * | 12/2004 | Olstad | 600/437 |
| 2005/0038355 A1 * | 2/2005 | Gellman et al. | 600/564 |
| 2005/0085715 A1 * | 4/2005 | Dukesherer et al. | 600/424 |
| 2005/0107688 A1 | 5/2005 | Strommer | |
| 2005/0197557 A1 | 9/2005 | Strommer et al. | |
| 2005/0197566 A1 | 9/2005 | Strommer et al. | |
| 2006/0058647 A1 | 3/2006 | Strommer et al. | |
| 2007/0173861 A1 | 7/2007 | Strommer et al. | |
| 2008/0091171 A1 | 4/2008 | Strommer et al. | |
| 2008/0132911 A1 | 6/2008 | Sobe | |
| 2009/0030307 A1 * | 1/2009 | Govari et al. | 600/424 |
| 2009/0182224 A1 | 7/2009 | Shmarak et al. | |
| 2009/0198298 A1 * | 8/2009 | Kaiser et al. | 607/17 |

* cited by examiner

*Primary Examiner* — Vani Gupta
(74) *Attorney, Agent, or Firm* — Dykema Gossett PLLC (57) ABSTRACT

A method for detecting when a tool contacts a wall of a region of interest includes the steps of: tracking the motion of the tool and creating a tool motion profile; calculating a correlation value representative of the correlation between the tool motion profile and a wall motion profile indicative of the motion of the wall; and determining when the correlation value exceeds a threshold indicative of contact of the tool with the wall of the region of interest.

17 Claims, 5 Drawing Sheets

METHOD FOR DETECTING CONTACT WITH THE WALL OF A REGION OF INTEREST

BACKGROUND OF THE INVENTION a. Field of the Invention

The present invention relates generally to a method and related system for detecting contact with a wall of a region of interest.

b. Background Art

The background fields involve both medical tool-to-wall contact sensing techniques as well as medical positioning (or localization) systems, including applications of position and orientation (P&O) data obtained therefrom.

Generally, the visualization and treatment of organs and tissues has been advanced through the increasing use of catheter systems and their overall integration within medical positioning systems. Catheter systems are designed for the incorporation of various components to treat and diagnose ailments, as accomplished through the mapping of organs, sensing of thermal and electrical changes exhibited by a tissue (e.g., heart), as well as the application of energizing sources (such as radiofrequency, cryogenics, laser, and high frequency ultrasound) to tissue. Catheter systems generally include a portion that contacts the tissue or organ, or is inserted in an environment (e.g., heart chamber or vessel) to detect a number of parameters, such as for example, location of the tissue, contact or pressure exerted on the tissue, electrophysiological attributes of the tissue, or other type of parameters that aid in the evaluation or treatment of the organ or tissue.

Accordingly, the ability to detect when a tool (e.g., catheter tip) makes contact with a wall of a region of interest allows the physician to know, for example, when to stop advancing the tool (in order to prevent bends and/or ruptures in the wall of the region of interest). Additionally, when electrophysiology measurements or ablation are performed, the ability to detect when a tool makes contact with a wall of a region of interest allows the physician to know when to perform the measurement or ablation.

There are a number of techniques used for detecting when a tool has made contact with a wall or other object within a body. Such techniques include, but are not limited to, electrical-based sensing via an analysis of measured electrical parameters taken through the wall tissue and contact-sensing based on pressure and flow measurements transmitted by a sensor or via optical means (as described in greater detail below). However, each of these methods have their inherent limitations and as a result, none of the known approaches provide a truly robust solution for tool-to-wall contact detection. For example, electrophysiological catheters rely primarily on the measurement of electrical parameters to determine if contact is achieved between a tool and a region of interest. Electrical evaluation is one of the most effective methods for determining contact when using an electrophysiological catheter, but such technique is limited to the use of the specific catheter type (i.e., the type having a tip electrode). Alternatively, other types of catheters (i.e., non-electrophysiological) require the detection of contact sensing through other means, such as through the use of pressure or flow sensors. Pressure (or force) sensors may be positioned within a catheter such that physical contact with the wall is detected through the sensor. This method obviously provides limited results depending on the location and/or placement of the sensor within the catheter or other medical tool. Another method of detecting contact by a tool or changes in environment surrounding a tool (i.e., in a cavity verses in contact with a body) includes the use of flow sensors that measure the relative "flow" and/or movement of fluid (e.g., blood) around the catheter, such as for example, relative movement due to hemodynamic forces. Contact of the catheter with an organ wall effectively decreases the relative flow measurement, indicative of contact of the catheter with a wall or body. Each of these methods may be unpredictable, therefore it is desirable to have additional methods for determining when contact is made by a tool with a wall of a region of interest.

As to positioning systems, a number of systems and methods are used in the field of medical imaging and detection to determine the position and orientation of medical tools, either diagnostic or therapeutic, within the body, for example, as seen by reference to U.S. Pat. No. 7,386,339 entitled "MEDICAL IMAGING AND NAVIGATION SYSTEM" to Strommer et al., hereby incorporated by reference in its entirety. Strommer et al. disclose a medical imaging and navigation system that has a capability for constructing and displaying three-dimensional images of moving organs, synchronously with the actual movement of these organs and synchronously with an invasive medical tool, such as a catheter. The system includes a medical positioning system for ascertaining the location and orientation of multiple medical positioning system sensors, including for example, a sensor associated with a surgical tool, and a sensor attached to the body of the patient for providing a positional reference ("Patient Reference Sensor", or PRS). When a physician inserts the tool into the body of the patient, the system detects the location and orientation of the medical positioning system sensor that is mounted on the tool. In addition, the system also detects movements of the patient using the PRS (e.g., patient body movements and respiration induced movements), which may be used for motion compensation. However, Strommer et al. do not teach use of the position and orientation readings to detect tool-to-wall contact.

Accordingly, there is a need for a contact sensing system that minimizes or eliminates one or more of the problems set forth above.

BRIEF SUMMARY OF THE INVENTION

The present disclosure describes a method for detecting when a tool makes contact with a region of interest. A tool may be guided through a lumen, such as a vascular region (e.g., vein, artery) of a body or patient towards a particular region of interest, such as the atria or ventricles of the heart. The method includes the step of tracking the motion of a tool and creating a tool motion profile. A wall motion profile is indicative of the motion of the wall of the region of interest. The wall motion profile may be created based on predetermined motion pattern data for an identified region of interest. Alternatively, or in addition to predetermined data, the region of interest motion data may be obtained using one or more motion measurement strategies, for example, through the use of image analysis, electrical parameter measurement including electro-cardiogram analysis and/or position sensor-based measurement. The region of interest motion data may then be used to create the wall motion profile. A correlation value is calculated representative of the correlation between the tool motion profile and the wall motion profile. The method further includes the step of determining when the correlation value exceeds a threshold indicative of tool-to-wall contact. In further embodiments, once the correlation value exceeds the threshold level, a contact indicator is activated to indicate to the user that tool-to-wall contact is detected. Contact indicators may include visual, auditory, tactile, electrical, or other signal indicators and combinations thereof that are known.

The present disclosure further describes a method for detecting when a catheter contacts a wall of a heart cavity. The method includes the step of tracking the motion of a catheter and creating a catheter motion profile. The method further includes calculating a correlation value based on the catheter motion profile and a wall motion profile indicative of the motion of the wall of the heart cavity. Moreover, the method includes the step of determining when the correlation value exceeds a threshold indicative of catheter-to-heart wall contact. The wall motion profile may be created based on predetermined motion pattern data reflective of the heart wall motion. Alternatively, or in addition to such predetermined data, one or more motion measurement strategies, such as for example image analysis, electrical parameter measurement including electro-cardiogram analysis and/or position sensor-based measurement may be used to create the wall motion profile based on measured heart wall motion data.

The present disclosure further describes a system for detecting when a tool contacts a wall of a region of interest. The system includes a tool having a sensor associated with the tool for tracking the motion of the tool; a medical positioning system for determining the position of the tool within a body; a main control unit; and a contact indicator for signaling when a threshold level has been exceeded, thereby indicating contact between the tool and the wall of the region of interest. The main control unit is configured to create a tool motion profile based on evaluating the movement of the tool. The main control unit calculates a correlation value representative of the correlation between the tool motion profile and a wall motion profile, the wall motion profile being reflective of the motion of the wall. The main control unit further determines when the correlation value exceeds a threshold indicative of tool-to-wall contact. Once the threshold level is exceeded, a signal indicator indicates that contact has been made by the tool with the region of interest.

The foregoing and other aspects, features, details, utilities, and advantages of the present invention will be apparent from reading the following description and claims, and from reviewing the accompanying drawings.

DETAILED DESCRIPTION OF THE INVENTION

In general, the instant disclosure describes a system and method for detecting contact of a medical tool with a region of interest, such as for example, a catheter within a heart cavity. For purposes of this description, similar aspects among the various embodiments described herein will be referred to by the same reference number. As will be appreciated, however, the structure of the various aspects may be different among the alternate embodiments.

The term "position" herein below, refers to the location of a point in space, or a combination thereof. The term "lumen" and/or "organ" herein below, refers to a tubular structure of the human patient or the operated animal, such as an artery, vein, cardiac vessel, heart chamber, brain vessel, part of the urogenital system, nephrotic system, hepatic system, bronchus tree, and the like.

Figure 1:
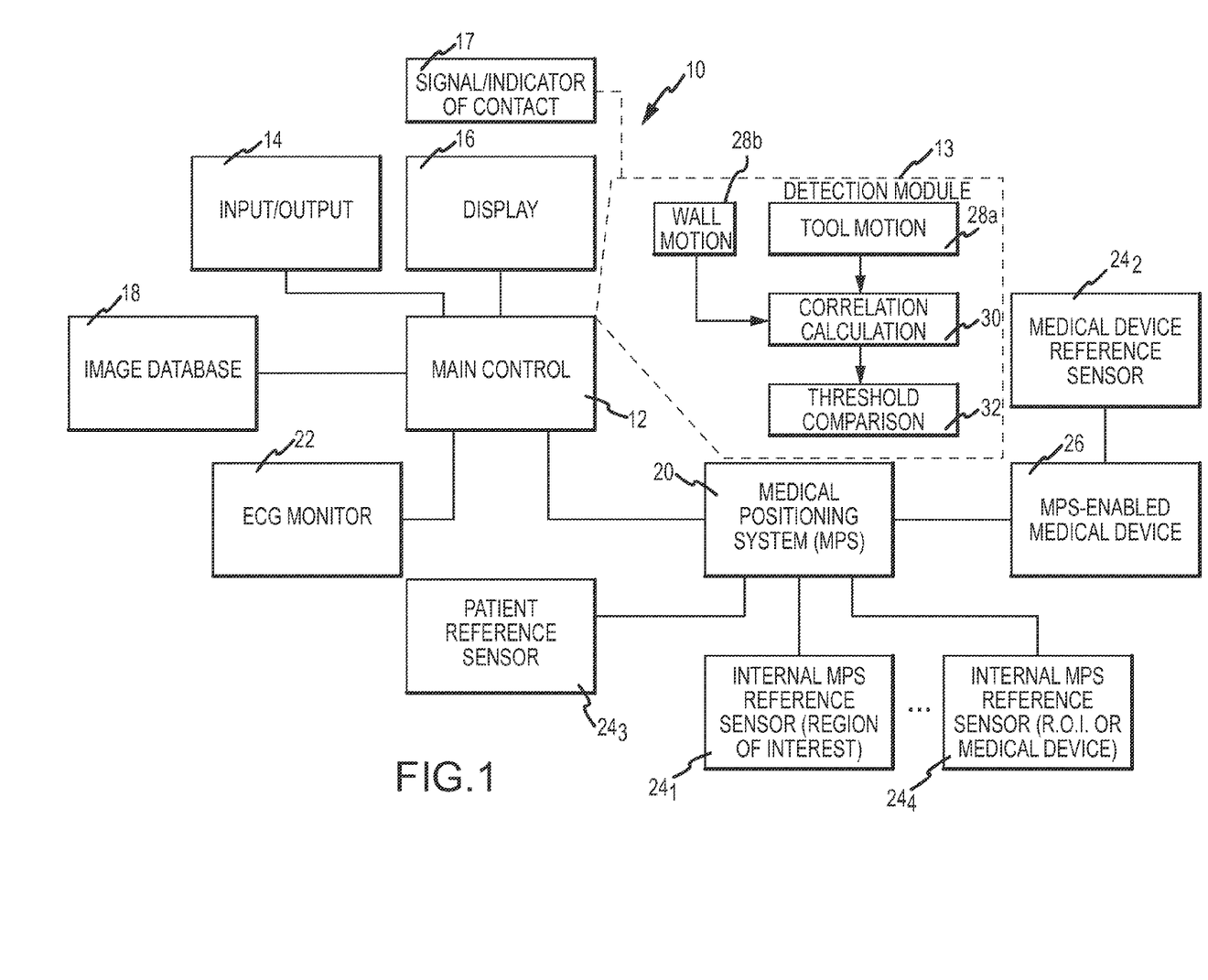
FIG. 1 is a schematic illustration of a system, constructed and operative in accordance with an embodiment of the disclosed technique.

FIG. 1 is a diagrammatic view of a system 10 in which aspects of the invention may be embodied. It should be understood that while embodiments will be described in connection with a magnetic field-based positioning system deployed in connection with a fluoroscopy-based imaging system, such an embodiment is exemplary only and not limiting in nature.

The system 10, as depicted in FIG. 1, includes a main control 12 having various input/output mechanisms 14, a main display 16, a tool-to-wall contact signal/indicator 17, an image database 18, a localization system such as a medical positioning system 20, an electrocardiogram (ECG) monitor 22, a plurality of medical positioning system position reference sensors designated $24_1$, $24_2$ and $24_3$, and an medical positioning system-enabled medical device 26, which itself includes the position reference sensor $24_2$ and may be alternately referred to herein as a medical tool or simply a "tool". The medical positioning system-enabled device 26 may be any interventional device or delivery tool. An additional medical positioning system position reference sensor designated $24_4$ may further be included that is coupled or used in connection with either the region of interest (ROI) or with further medical positioning system-enabled medical devices. It should be understood, however, that certain embodiments may contain fewer than three of the medical positioning system sensors $24_1$, $24_2$ and $24_3$. For example, as described below, certain embodiments may omit sensor $24_1$ (associated with the ROI) and instead use predetermined data (e.g., predetermined data 62), such as imaging data, for developing a ROI motion profile. In addition, as also described below, certain embodiments may omit sensor $24_3$, which may take the form of a patient reference sensor (PRS) useful for motion compensation. Other variations are possible.

The main control 12, in a computer-implemented embodiment, is programmed to perform a plurality of functions through the use of a detection module 13. Module 13 includes a tool motion profile block 28a, a wall motion profile block 28b, a correlation calculation block 30 configured to determine the correlation between the tool and wall motion profiles, and a threshold comparison block 32. Generally, the main control 12 detects contact when the tool motion sufficiently correlates to the wall motion. The input/output mechanisms 14 may comprise conventional apparatus for interfacing with a computer-based control, for example, a keyboard, a mouse, a tablet or the like. The display 16 may also comprise conventional apparatus. The tool-to-wall contact signal/indicator 17 may be comprised of various signal indicators including, but not limited to, visual, auditory, tactile, electrical and other types or combinations of methods used to provide a signal to a user. Indicator 17 may be provided in connection with a display 16 or may be separate.

When determining contact of a tool with a region of interest, imaging of the region of interest may be useful in a number of ways. For example, the images may be used (1) to assess the motion of the region of interest or (2) to be used as a display reference on which the indication of contact of the tool may be projected. The image database 18 may therefore be configured to store image information relating to the region of interest for at least such purposes. Images may be acquired through any imaging modality, now known or hereafter developed, for example fluoroscopic imaging, X-ray, ultra-sound, computerized tomography, nuclear magnetic resonance or the like.

The medical positioning system 20 is configured to acquire positioning (localization) data (i.e., position and orientation—P&O) of one or more medical positioning system sensors. The P&O may be expressed as a position (i.e., a coordinate in three axes X, Y and Z) and/or orientation (i.e., an azimuth and elevation) of the magnetic field sensor in the magnetic field relative to a magnetic field generator(s)/transmitter(s). In one embodiment, such P&O information is obtained in a substantially continuous fashion from each medical positioning system sensor. The P&O readings may then be compiled to generate P&O data sets. The tool motion and wall motion profiles may be based solely on the respective P&O data sets generated by respective medical positioning system sensors. Each of the medical positioning system sensors, $24_i$, are provided in association with various functions and may be configured to collect information for designated purposes.

The internal medical positioning system position reference sensor $24_1$, if used, is associated with a moving region of interest (ROI) in the body, which may be a moving organ, and more specifically may be the heart and/or chambers or portions thereof (e.g., atria). The internal position reference sensor $24_1$ is associated with the ROI in such a way that it will move together with the moving ROI. Thus, the P&O information derived therefrom will fairly indicate the motion of the region of interest.

The medical device reference sensor $24_2$ (best shown in FIG. 3) is associated with the medical tool 26 (e.g., a catheter). The reference sensor $24_2$ may be installed near the tip of the tool, i.e. catheter tip, parallel to the main axis of the medical tool. As indicated, the position of the tool 26 is determined based on the P&O information derived from the reference sensor $24_2$. Therefore, the position of the tip or the portion of the catheter making contact, may be derived from P&O readings provided by the sensor and/or predetermined information (e.g., distance) relating to the sensor and catheter tip location.

The patient reference sensor (PRS) $24_3$ (if present) is configured to provide a positional reference of the patient's body so as to allow motion compensation for gross patient body movements and/or respiration-induced movements, as described above. The PRS $24_3$ may be attached to the patient's manubrium sternum, a stable place on the chest, or other location that is relatively positionally stable. Motion compensation approaches may be used as disclosed in U.S. Pat. No. 7,386,339 referred to above as well U.S. Pat. No. 7,343,195 (application Ser. No. 09/949,160 filed Sep. 7, 2001) entitled "METHOD AND APPARATUS FOR REAL TIME QUANTITATIVE THREE-DIMENSIONAL IMAGE RECONSTRUCTION OF A MOVING ORGAN AND INTRA-BODY NAVIGATION" to Strommer et al., the disclosures of both U.S. Pat. Nos. 7,386,339 and 7,343,195 being hereby incorporated by reference herein in their entireties.

One or more additional, optional internal position sensors may be provided, for example, as shown by sensor $24_4$. The additional one or more sensors $24_4$ may be associated with either or both of the (1) the moving region of interest; or (2) the medical tool 26. The additional sensors $24_4$, may be configured to provide information allowing medical positioning system 20 to produce additional data points (P&O readings) with respect to either the moving region of interest or medical device, as the case may be, thereby providing addition information concerning their respective motions over time.

The electrocardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. The ECG signal may be used by the main control 12 for ECG synchronized play-back of a previously captured sequences of images (cine loop). The ECG monitor 22 and ECG-electrodes may comprise conventional components. In lieu of or in addition to the ECG, other known devices may be used in connection with system 10 to collect information related to the movement of the region of interest to generate wall motion data. Moreover, with the availability of the ECG signal and a PRS position signal, the main control 12 may further compensate for various movements, including but not limited to, overall global body movements (e.g., patient movement including respiratory compensation), local movements (e.g., catheter movement through hemodynamic forces), and physician movement.

Figure 2:
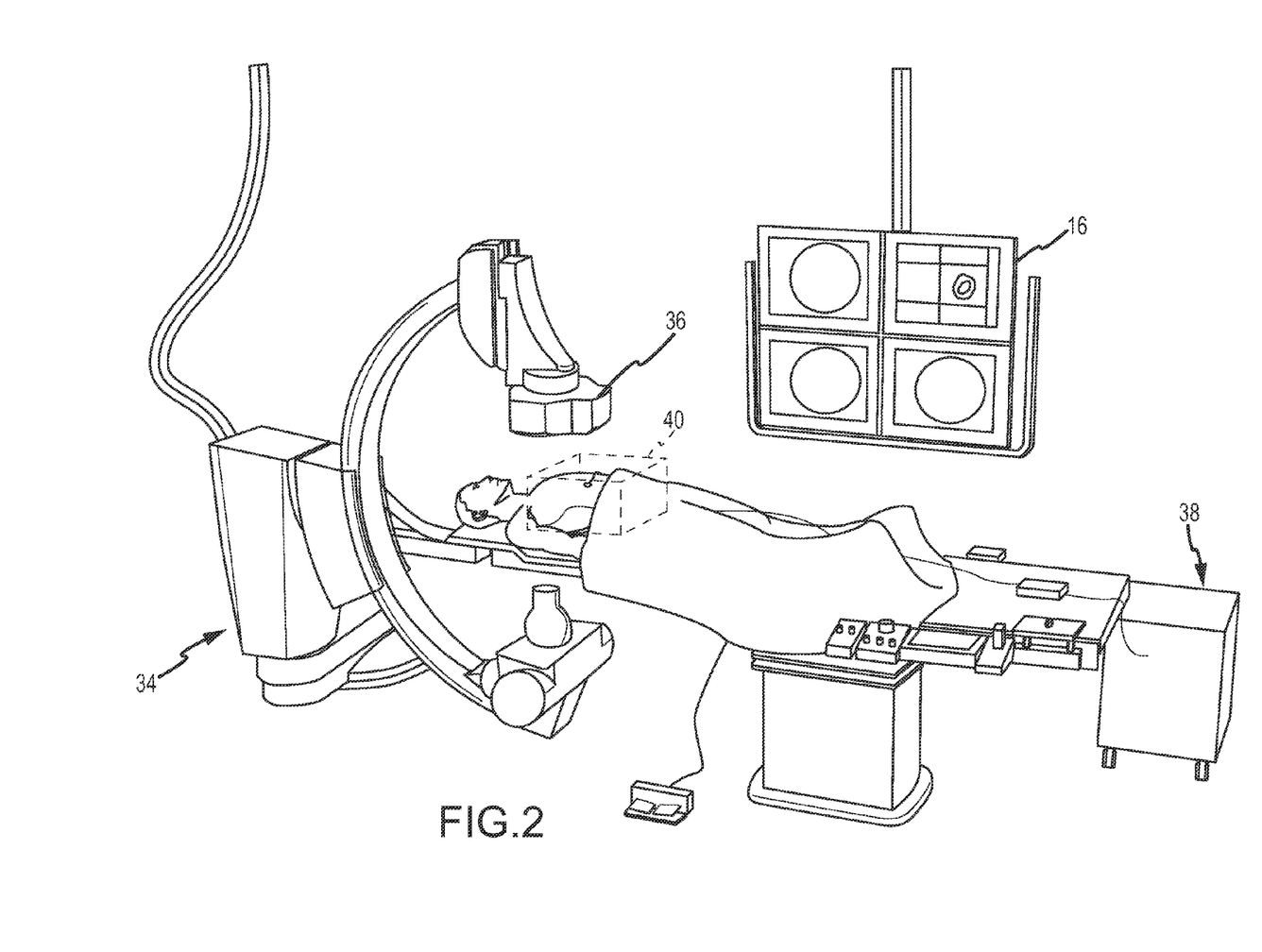
FIG. 2 is a diagrammatic view of an embodiment of the invention.

FIG. 2 is a diagrammatic view of an integrated imaging and processing system in which embodiments may be used. Each of the described components may thus be integrated into an imaging and processing system that is designed for use in a surgical and/or evaluation setting with a patient. More specifically, system 10 may be incorporated into an fluoroscopic imaging system 34, which may include commercially available fluoroscopic imaging components (i.e., "Catheter Lab"). The medical positioning system 20, in a magnetic field-based positioning embodiment, includes a magnetic transmitter assembly (MTA) 36 and a magnetic processing core 38 for determining position and orientation (P&O) readings. The MTA 36 is configured to generate the magnetic field(s) in and around the patient's chest cavity, in a predefined three-dimensional space designated a motion box 40 in FIG. 2. The medical positioning system sensors $24_i$ (where i=1, 2, . . . , n) as described above are configured to sense one or more characteristics of the magnetic field(s) and when they are in the motion box 40 they each generate a signal that is provided to the magnetic processing core 38. Accordingly, the medical positioning system sensors $24_i$ may each comprise one or more magnetic field detection coil(s), although it should be understood that other configurations are possible. The sensors 24 are configured to detect one or more characteristics of the magnetic field(s) in which they are disposed and generate an indicative signal, which is further processed to obtain the P&O thereof. For one example of a sensor, see U.S. Pat. No. 7,197,354 entitled SYSTEM FOR DETERMINING THE POSITION AND ORIENTATION OF A CATHETER issued to Sobe, hereby incorporated by reference in its entirety. The processing core 38 is responsive to these detected signals and is configured to calculate respective three-dimensional position and orientation (P&O) readings for each medical positioning system sensor $24_i$ in the motion box. Thus, the medical positioning system 20 enables real-time tracking of each sensor $24_i$ in three-dimensional space. Such position readings and/or P&O may be used to determine a tool motion profile (as generated by sensor $24_2$) or the wall motion profile (as generated by sensor $24_1$). In the illustrated embodiment, the positional relationship between the image coordinate system and the medical positioning system coordinate system may be calculated based on a known optical-magnetic calibration of the system (e.g., established during setup), since the positioning system and imaging system may be considered fixed relative to each other in such an embodiment. A "weighted" combination of information derived by the medical positioning system sensors in connection with the images obtained from the imaging system may be used to establish the position of the tool in relation to the wall of the region of interest. However, for other embodiments using other imaging modalities, including embodiments where the image data is imported from an external source, a registration step may need to be performed initially. One exemplary embodiment of an medical positioning system 20 will be described in greater detail below in connection with FIG. 6.

Figure 3:
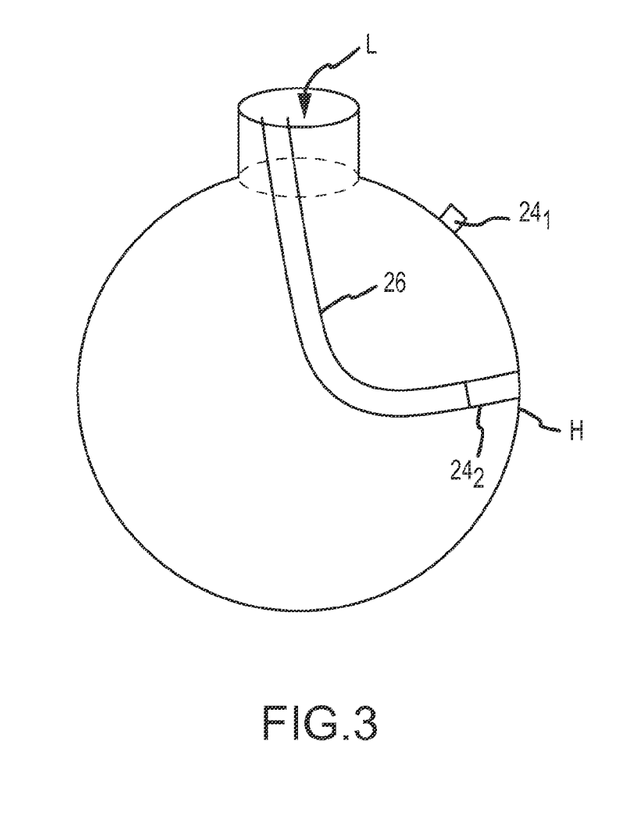
FIG. 3 is a schematic illustration of a two-dimensional image of an organ showing the relative positioning of a tool.
Figure 4:
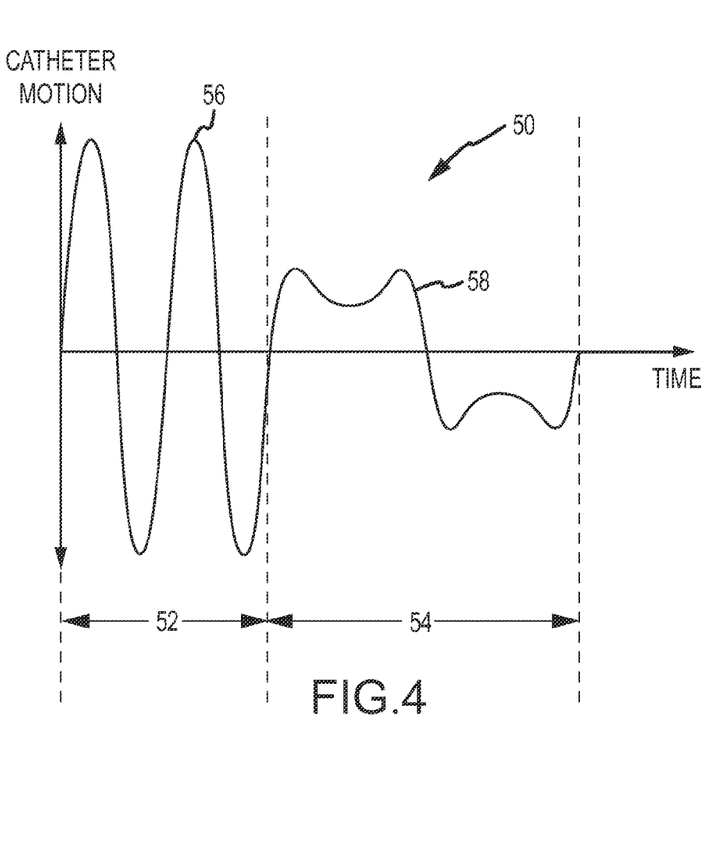
FIG. 4 is a graphical representation of the motion of the tool versus time in non-contact and contact phases.

In accordance with the disclosed method and corresponding system, FIGS. 3 and 4 further illustrate the use of an medical positioning system for detecting contact of a device with a region of interest. For illustrative purposes only, FIG. 3 shows catheter 26 inserted into the right atrium of the heart (H) via an insertion region of the lumen (L) (i.e., the Superior Vena Cava). Medical positioning system sensor $24_2$ is coupled to the catheter 26 and relays signals indicating the relative position and/or orientation of the catheter 26. As a result, position and/or orientation data or medical positioning system data sets provided by medical positioning system 20 may be recorded. Medical positioning system sensor $24_2$ is located at the distal tip of the catheter. Hemodynamic forces, such a blood flow or blood pressure, may be exerted on catheter 26 thereby impacting the overall movement of catheter 26. Based on the series of position and/or orientation readings derived from sensor $24_2$, the motion (i.e., position and orientation) of catheter 26 is determined. The series of time-based position readings will reflect the motion of the medical tool. For example in the case of a catheter in a heart cavity, the position of the catheter will have frequency content, with contributions from (i) the beating of the heart, (ii) the patient breathing (i.e., respiration) as well as (iii) other position influences (e.g., position changes of the catheter resulting from the physician or a robotic system intentionally moving the catheter). Accordingly, frequency components of the catheter motion 26 may therefore also be calculated.

Generally, a tool motion profile may be created based on the collected data sets, as illustrated by the representation of the catheter motion within FIG. 4. Through evaluation of the motion of the tool by reference to the continuous position of the medical positioning system sensor coupled to the tool, a tool motion profile may be created that reflects the relative position and movement of the tool (e.g., catheter).

FIG. 4 is a position-versus-time diagram provides a graphical representation of the motion of the tool motion in non-contact and contact phases. As reflected in representation 50, the relative position of the tool is detected and identified via time stamped position and orientation (P&O) readings. These P&O readings may form medical positioning system data sets that may be recorded (as noted above) for comparison. Accordingly, that portion 56 of the tool (i.e., catheter) motion over time interval 52 is reflected by a continuous smooth motion, with no significant, high frequency content. For illustrative purposes only, portion 56 is indicative of no-contact between the tool and the region of interest. Alternately, portion 58 over time interval 54 indicates contact between the tool and the region of interest. The higher frequency content present in tool motion 58 reflects contact of the tool with the wall of organ (H). This is because the high frequency movement with the muscle contraction are directly detected by virtue of the tool-to-wall contact. The overall frequency of the tool motion may include frequency components for both heart rate motion and respiratory motion. Accordingly, the frequency component attributed to heart rate motion may be determined by calculating the respiratory frequency component (i.e., through the use of the PRS, $24_3$), and subtracting from the overall frequency measurements. Depending on the area of contact and/or position of the tool within the organ, the frequency may vary. Changes in frequency may be seen, such as for example, frequency measurements based on contact with an internal wall or external wall of a heart chamber, vessel wall, or any other areas. Visually, contact of a tool with the region of interest is shown as abrupt changes in the position versus time graph.

Figure 5:
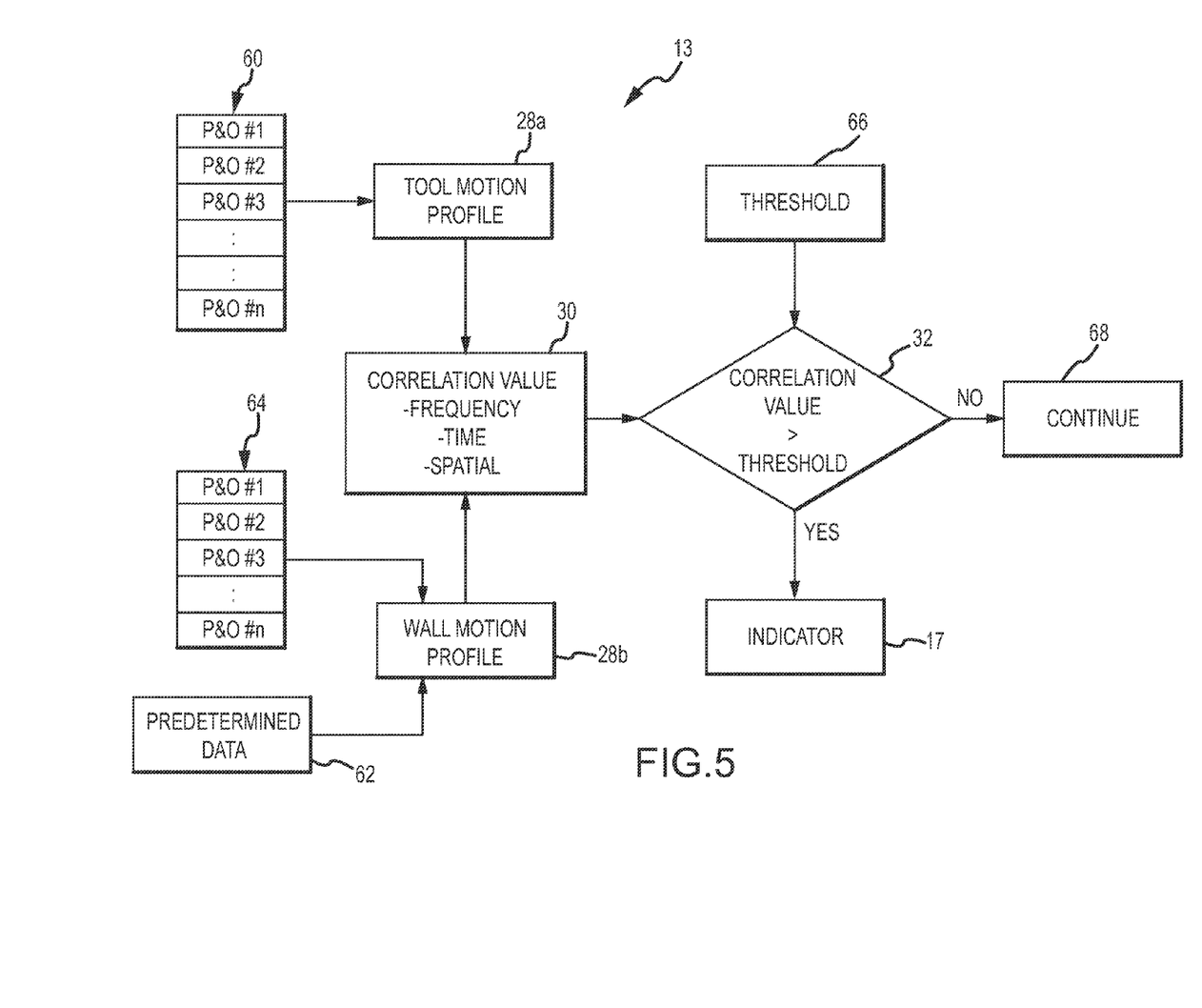
FIG. 5 is a schematic and block diagram view of one exemplary embodiment of a main control unit as shown in block form in FIG. 1.

FIG. 5 is a schematic and block diagram showing in greater detail, the detection module 13 of FIG. 1. The operation of blocks, 28a, 28b, 30 and 32, results in 1) collection of data (P&O data sets) to create a) a wall motion profile and b) a tool motion profile; 2) the determination of a correlation value based on a comparison between the tool motion and wall motion profiles; and 3) a threshold level comparison with the correlation value to determine contact. Ultimately, either contact of the tool with a region of interest is detected and indicated through the use of a tool-to-wall contact indicator, or the collection of P&O data continues.

A. Tool Motion Profile

The tool motion profile block 28a of the main control unit 12 is configured to produce data indicative of the motion of the tool 26. The relative position and orientation of the tool within a lumen is determined through the interaction of the medical positioning system sensors and the collection of data sets from the medical positioning system sensors. As shown in FIG. 5, for simplicity, one such data set labeled P&O data set 60 is provided with respect to the motion of the tool 26. It should be understood that plural medical positioning system sensors may be used to track the motion of the tool, resulting in plural P&O data sets. The data set 60 is then processed by block 28a and the motion of the tool is determined. As a result, the movement of the surgical tool within a volume of the body may be continuously analyzed by main control 12 (via block 28a) over a period of time. One of the medical positioning system sensors, $24_2$, is coupled to the medical device, such as for example, tools used for mapping, surgical procedures (i.e., ablation), or other medical procedures. The plurality of P&O readings (i.e., P&O #1 . . . P&O #n) in tool data set 60 may be processed by block 28a to extract or examine for analysis any number of aspects or components of the tool motion, including position, orientation, frequency components, velocity, trajectories as measured in distance and/or time, as well as various combinations, all in order to generate the overall tool motion profile by tool motion block 28a.

The medical positioning system-enabled medical device 26 (i.e., surgical tool) may be any medical device and/or tool that would be disposed within a lumen of a body. More particularly, device 26 may be selected from any type of surgical device used for insertion within a lumen or cavity, such as, for example, a catheter, a dilator, an introducer, a sheath, a substance delivery unit, a stent, a CRM pacing lead, or any other medical device. Although various medical devices may be employed, the present invention may also be directed to the use of a catheter, in particular, those used for mapping and contact sensing. Moreover, the disclosed embodiments may be used with both electrode and non-electrode carrying catheters. The catheter traditionally used in connection with medical positioning system 20 is a catheter fitted with an medical positioning system sensor positioned relative to the distal end of the catheter tip and configured to provide relative position and orientation signals to medical positioning system 20.

In order to determine the relative position and orientation of the catheter over time and as a result, the relative movement of the catheter within the lumen, the medical positioning system sensors $24_i$ work in connection with one another providing feedback (signals) to medical positioning system 20 over basic time increments. The time increments between consecutive medical positioning system positioning data samples, such as for example, every 8 mSecs, allow for a substantially continuous relay of information to medical positioning system 20.

B. Wall Motion Profile

The wall motion profile block 28b of control unit 12 is configured to produce data indicative of the motion of the wall of the region of interest. The movement of the organ (H) or the wall of the organ (i.e., ROI) is determined and described in a wall motion profile. A wall motion profile, as shown in FIG. 5, is generated based on data, either predetermined and/or acquired in real-time, of the overall motion of the region of interest. More specifically, the region of interest (ROI) motion data may be based on either position and orientation (P&O) readings collected for the ROI, predetermined data for the ROI, or a combination of both.

In an embodiment, the wall motion profile may be based on predetermined data, shown as block 62. The predetermined data may be collected prior to the procedure, based on standard parameters known within the medical field, actual and/or real-time measurements collected from the patient, or a combination of standard and actual measurements. The wall motion data/profile may be based on predetermined information that is standard or resulting from a pre-procedure evaluation. For example, the motion of the heart (and chambers thereof) is fairly well understood in the art, and such known information can immediately provide a useful baseline. The predetermined data may then be calibrated during the course of the procedure based on actual ROI motion patterns (e.g., if heart motion, then through ECG) to ensure more accurate measurements and data recording. Alternately, the predetermined motion pattern data may be based on motion pattern data from patients other than the actual patient undergoing the procedure. As a result, the predetermined motion pattern data may be based on averages, means, or other weighted measurements reflective of organ pattern data that is collected over time for patients, such as those that have similar physical characteristics.

In another embodiment, the motion of the ROI may be determined based on actual or real-time motion patterns detected by various means, such as, for example the use of a region of interest sensor, $24_1$. One or more of the internal position reference sensors (e.g., sensor $24_1$) are located in the vicinity of the region of interest, or are otherwise associated with the region of interest (e.g., affixed) such that the internal medical positioning system reference sensor, $24_1$, moves together with the region of interest over time. Generally, associating the sensor $24_1$ with the region of interest (ROI) may be done in any one or more ways including but not limited to: (1) placing the sensor $24_1$, or an interventional device like a catheter carrying the sensor $24_1$, in an anatomical area where it is held by the anatomy itself, for example, a catheter that has been maneuvered in a tubular organ like the coronary sinus; (2) fixing the sensor $24_1$, or an interventional device like a catheter carrying the sensor, to the anatomy in the region of interest using a fixation mechanism, active or passive, for the duration of the procedure; (3) holding the sensor $24_1$, or an interventional device like a catheter carrying the sensor, in steady contact with the anatomy in the region of interest; and (4) placing sensor $24_1$ (or interventional device carrying the sensor) in a non-medical positioning system-enabled device that is in turn affixed to the anatomy in the region of interest. As to approach (2), where the region of interest is the heart, an example may include placing the sensor $24_1$ epicardially in the surface of the heart. As to approach (3), an example may include associating the sensor $24_1$ with a catheter that is maneuvered into steady contact with the heart interior. As to approach (4), an example may include placing an medical positioning system-enabled guidewire (having the sensor $24_1$) in the lumen of a pacing lead that is in turn affixed to the tissue of a heart chamber.

In another embodiment, the motion of the ROI may be deduced from known correlation with a signal other than a motion profile signal. For example, the motion profile of a cardiac chamber wall may be related through known models to electrical activity signal such as ECG.

As the region of interest moves, the medical positioning system 20 acquires a series of location (i.e., position and/or orientation) readings from the sensor. The series of collected P&O readings, for simplicity, is shown as a single wall P&O data set 64 in FIG. 5. In another embodiment, the block 28b is configured to determine the motion of the ROI based on a combination of actual (i.e., P&O data set 64) and predetermined (i.e., data 62) patterns.

The above described ROI motion data (i.e., predetermined data 62, P&O data 64 or a combination thereof) may be obtained using a selected motion measurement strategy suited to the motion of the region of interest (e.g., right atrium). The motion measurement strategy may be selected from the group including image analysis, electrical parameter measurements including electro-cardiogram analysis, positioning sensor-based measurements, or other means (now known or hereafter developed) for collecting information reflective of the motion of the region of interest. Moreover, spatial analysis, such as through the use of repetitive analysis, cyclicity, and trajectory of motion, either based on distance or time, together with the use of frequency matching can be used to determine the motion of the region of interest. Accordingly, each of these strategies may be taken to collect information reflecting the motion of the organ (H) wall. As previously discussed, reference sensor $24_1$ may be disposed relative to the organ or region of interest, such that the position signals provided by the reference sensor create an actual wall motion profile reflective of the real-time movement of the ROI.

Moreover, the image database 18 may be used to provide real-time and/or pre-acquired images of the region of interest. In some instances, image data from database 18 may be sufficient to determine the wall motion profile (e.g., in smaller vessels, like a coronary artery/vessel, coronary sinus where the image data typically clearly reveals the motion of the region of interest). In other embodiments, however, particularly where the image data may not show the motion of the region of interest clearly enough to develop an adequate motion profile (e.g., heart cavity), the motion of the region of interest may be augmented by real-time motion data provided by the medical positioning system 20 by virtue of associating a medical positioning system sensor with the moving region of interest. The motion profile 28b is configured in such other embodiments to develop the wall motion profile based on the respective contributions derived from both image data and medical positioning system (P&O) data. These two inputs may be weighted in a manner so as to reduce variation or deviation from the actual motion of the region of interest. Accordingly, and without loss of generality, and depending on the region of interest, such as for example heart chambers, images may be collected using a number of methods and analyzed in combination with collected P&O data to provide a composite motion profile for the region of interest. Then, as described elsewhere, the wall motion profile can be compared with the tool motion profile to determine the degree of correlation to thereby detect tool-to-wall contact.

Whatever input data the wall motion profile block 28b is configured to use (or is available to use), it is further configured to perform or process such data to extract or examine for analysis any number of aspects or components of the wall motion including position, orientation, frequency components, velocity, trajectories as measured in distance and/or time, as well as various combinations. Preferably, the extracted or examined aspects are the same as those prepared by the tool motion block 28a to allow like comparisons by the block 30. Moreover, any errors in the collected data for either the tool motion or wall motion may be compensated for through known methods.

C. Correlation

Once the tool motion and wall motion profiles are produced (above), the correlation block 30 operates to determine a correlation value between the two profiles. Correlation calculation block 30 is configured to determine the level of correlation (i.e., percent (%) comparison) between the tool motion profile generated by tool motion block 28a, and the wall (ROI) motion profile generated by wall motion block 28b. Accordingly, determining the correlation value through block 30 involves comparing at least one of the (i) frequency-based components, (ii) time-based components and (iii) spatial-based components of the tool motion profile with the corresponding components of the wall motion profile. Moreover, comparison between various components and combinations thereof may be used.

As indicated, various motion analysis methods may be used either individually or in combination with one another to determine the correlation value between the tool motion and wall motion of the region of interest. In one embodiment, the motion analysis method may include frequency-based analysis of the tool motion and wall motion, such that a correlation can be determined indicative of contact. As a result, a frequency-based comparison or correlation may be made such that a correlation between tool motion and wall motion is identified by determining whether a predetermined frequency component present in the wall motion is present in the tool motion. Moreover, the frequency component in the tool motion may be above the predetermined frequency component, thereby indicative of tool-to-wall contact. The frequency component of the tool motion, either near, equal to, or above the frequency component of the wall of the region of interest, may be used to indicate contact between the tool and wall of the region of interest. In an alternate embodiment, the tool motion and wall motion profiles may be determined based on the trajectories of each measured over a period of time. Each of the trajectories may be based on distance (i.e., mm), direction of movement, or combinations of each. The relative trajectories of both the tool motion and wall motion can be analyzed to determine the time-based and/or spatial-based position of each over a period of time. Consequently, each of the time-based and/or spatial-based positions of the tool and wall may be assessed on a common time-line, or over a similar period of time, to determine a relative degree of correlation. Moreover, repeating patterns of tool motion and wall motion trajectories may be determined in order to identify repetitive cycles of motion between the tool and wall motion trajectories indicative of tool-to-wall contact. Ultimately, comparison between the tool motion and wall motion is performed to obtain a correlation value.

D. Threshold Comparison and Detection

Once block 30 determines a correlation value block 32 compares the correlation value to a threshold (i.e., provided in block 66) to detect contact. Threshold comparison block 32 determines when the correlation value (%) exceeds a predetermined threshold level 66. The predetermined threshold level 66 may be selected by the user or may be modified based on the degree of contact (or confidence of contact) desired between tool 26 and ROI. Once the correlation value exceeds the threshold 66, for example 80%, the detection module 13 of control unit 12 generates an indication 17 that the tool has contacted the wall of the ROI. Although 80% is provided, this is merely exemplary in nature and may be modified according to the sensitivity of the system and the desired parameters set up by the user. Accordingly, the various threshold levels and correlation values may range anywhere from 60% and higher correlation, depending on the desired level of contact (or degree of confidence) of the tool with the wall of the ROI. In the event that the correlation value does not exceed the threshold, the collection of P&O data and the process performed by the detection module 13 may continue, as shown in the block 68.

E. Indication

The indication 17 of tool-to-wall contact may take many forms, depending on the kind of procedure and the reason for monitoring contact of the tool with a region of interest. Accordingly, the type of indicator used may vary depending on the type of tool being used and the area being contacted during the procedure, such as for example, a coronary vessel, a heart chamber (e.g., right atrium), the internal or external wall of the heart, or any other lumen/organ. The indicator 17 may include, but not be limited to, visual, auditory, tactile, electrical, or other types and combinations thereof. The type of indicator may be selected depending on the procedure being performed. For example, in one embodiment an internal signal (not human perceivable) may enable ablation energy to be delivered to the tool once contact is detected. In another example, a visual and auditory signal may be provided to the user, such that a projection of the real-time location information (P&O) of a medical device on previously recorded x-ray images or in the case of cine-loops (CL), may be provided on display 16 to indicate the location of the tool 26 in connection with the ROI. In a further example, once contact has been detected, the position of the contact point may be determined, for example, for mapping or ablating purposes. Once the position of the contact point is determined, this position and an indication of this position on imaging (e.g., real-time fluoroscopic image) may be compensated for errors originating in the motion of the region of interest.

Figure 6:
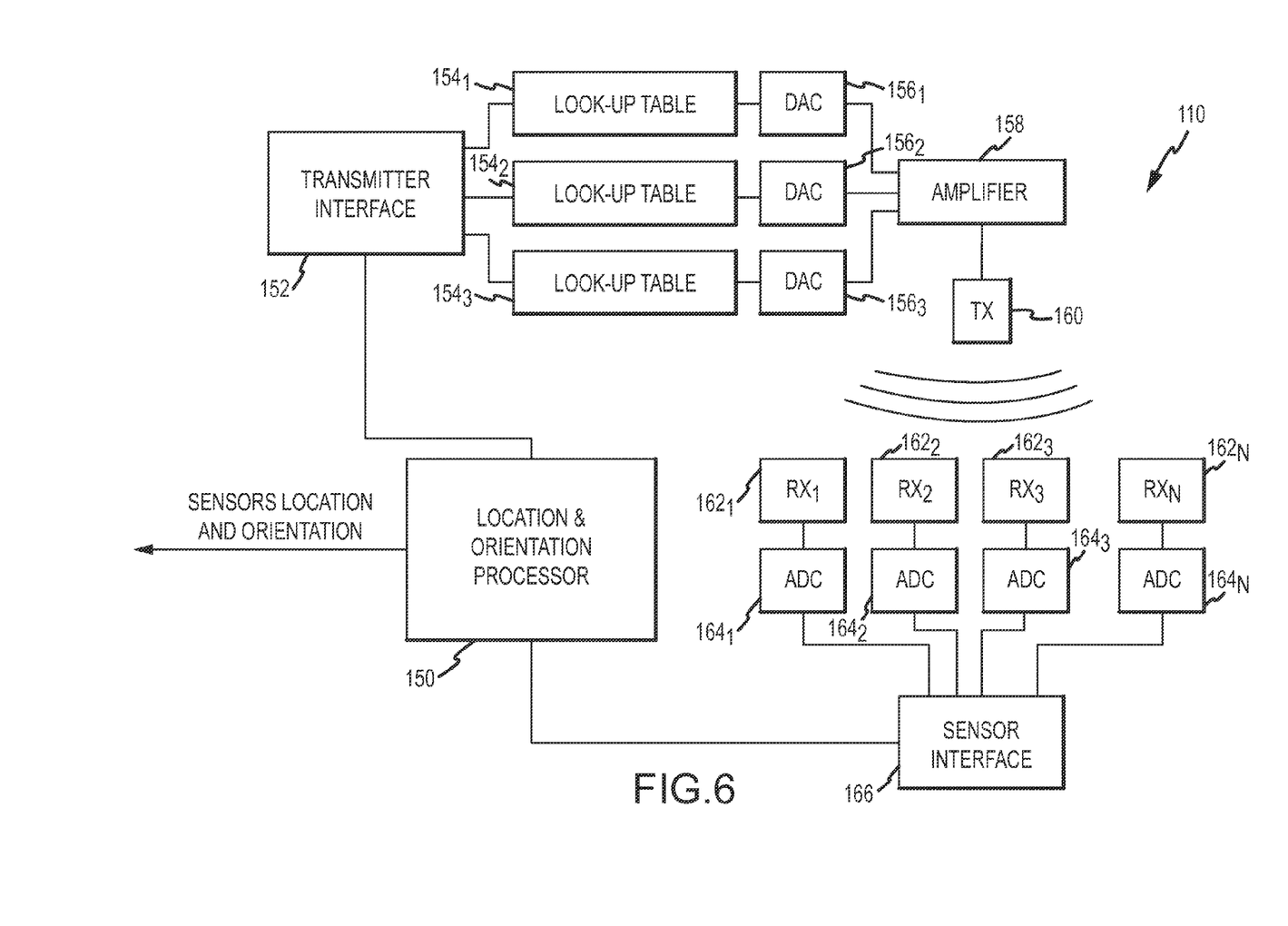
FIG. 6 is a schematic and block diagram view of one exemplary embodiment of a medical positioning system as shown in block form in FIG. 1.

FIG. 6 is a schematic and block diagram of one exemplary embodiment of medical positioning system 20, designated as an medical positioning system 108, as also seen by reference to U.S. Pat. No. 7,386,339, referred to above, and portions of which are reproduced below. It should be understood that variations are possible, for example, as also seen by reference to U.S. Pat. No. 6,233,476 entitled MEDICAL POSITIONING SYSTEM, also hereby incorporated by reference in its entirety. Alternately, various other navigational and visualization technologies, such as EnSite NavX™, as provided by St. Jude Medical, may be used in connection with the present invention. In general, magnetic-based positioning may be used in connection with the EnSite NavX™ system to augment and/or supplement each of the systems. For example, the EnSite NavX™ system may be used for mapping and visualization of an area or a particular region of interest, while the current system may be used to determine contact of the tool with the region of interest. As such, each of the systems may be used in combination with one another to correlate collected information and further provide an integrated system. The medical positioning system combines components that enable the sensing, transmission, and relaying of position and orientation information of each of the medical positioning system sensor to help facilitate the invention presently described. As previously discussed, it is the position and orientation of the medical positioning system sensors are collectively used to determine tool-to-wall contact.

Medical positioning system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of medical positioning system sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. Medical positioning system sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by medical positioning system sensors $162_1$, $162_2$, $162_3$ and $162_N$. Each of medical positioning system sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the medical positioning system sensors $162_1$, $162_2$, $162_3$ and $162_N$. Location and orientation processor 150 further determines distortion events and updates look-up tables $154_1$, $154_2$ and $154_3$, accordingly.

It should be further noted that system 10, particularly main control 12, as described herein, may include conventional processing apparatus known in the art, capable of executing instructions stored in an associated memory or other computer-readable medium that is accessible by main control 12, all performing in accordance with the functionality described herein. It is contemplated that the methods described herein, including without limitation the method steps described above, will be programmed in a preferred embodiment, with the resulting software being stored in an associated memory or a computer readable storage medium, and where so described, may also constitute the means for performing such methods. Implementation of the invention, in software, in view of the enabling disclosure, would require no more than routine application of programming skills by one of ordinary skill in the art. It is further contemplated that when the following methodology implemented in software is executed by main control 12, system 10 constitutes a special purpose machine.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for tracking a tool relative to a wall of a region of interest of a patient, the method comprising:
   tracking the motion of the tool, wherein the tool includes a positioning sensor at a distal end thereof configured to (i) sense one or more characteristics of a magnetic field produced by a medical positioning system and (ii) generate a signal indicative of a sensor position of the positioning sensor, and creating a tool motion profile including generating, using the medical positioning system in response to said signal, the tool position;
   calculating a correlation value representative of the correlation between the tool motion profile and a wall motion profile indicative of the motion of the wall, wherein calculating the correlation value comprises comparing at least one of the (1) frequency-based components, (2) time-based components and (3) spatial-based components of the tool motion profile with the corresponding at least one components of the wall motion profile, wherein the at least one component is the frequency-based component, and wherein said comparing includes determining whether a predetermined frequency component present in the wall motion is present in the tool motion;

determining when the correlation value exceeds a threshold, the correlation value exceeding the threshold being indicative of contact of the tool with the wall of the region of interest; and providing a contact indicator for signaling when the threshold level has been exceeded, therein indicating the tool is in contact with the wall of the region of interest.

2. The method of claim 1 wherein said step of tracking and creating the tool motion profile further includes:

generating time-based position data representative of the motion of the tool using the positioning sensor, said time-based position data comprising a plurality of tool positions at respective times.

3. The method of claim 1 further including:

creating the wall motion profile based on a predetermined motion pattern data for the region of interest.

4. The method of claim 3 wherein creating the wall motion profile includes:

obtaining motion pattern data from patients other than said patient.

5. The method of claim 1 further including:

selecting a motion measurement strategy for the region of interest from the group comprising image analysis, electrical parameter measurement including electrocardiogram analysis, and positioning sensor-based measurements;

obtaining measured region of interest motion data using the selection measurement strategy; and creating the wall motion profile based on at least the measured region of interest motion data.

6. The method of claim 5 wherein creating the wall motion profile is further performed based on one of (i) predetermined motion pattern data for the region of interest and (ii) a combination of the predetermined motion pattern data and the measured region of interest motion data.

7. The method of claim 5 wherein the selected motion measurement strategy comprises positioning sensor-based measurements, and wherein said obtaining measured region of interest motion data comprises:

providing said positioning sensor as a first positioning sensor and said signal as a first signal;

associating at least a second positioning sensor with the region of interest configured to sense one or more characteristics of the magnetic field produced by the medical positioning system and to generate in response thereto a second signal indicative of a second sensor position of said second positioning sensor wherein said medical positioning system determines said second sensor position of said second positioning sensor using said second signal; and generating time-based position data representative of the motion of the region of interest, said time-based position data includes a plurality of second sensor positions at respective times.

8. The method of claim 1 wherein the at least one component is the spatial-based component, and wherein said comparing includes:

determining a plurality of tool motion trajectories over a period of time to determine the relative time-based spatial positions of the tool;

determining a plurality of wall motion trajectories over said period of time to determine relative time-based spatial positions of the wall; and assessing the respective time-based spatial positions of the tool and wall on a common time-line to determine a degree of correlation.

9. The method of claim of 1 wherein the at least one component is the time-based component, and wherein said comparing includes:

determining a plurality of tool motion trajectories over a period of time to determine the relative time-based spatial positions of the tool;

determining a plurality of wall motion trajectories over said period of time to determine relative time-based spatial positions of the wall; and conducting cyclicity analysis to determine repetitive patterns of tool motion trajectories and the wall motion trajectories to identify correlation.

10. The method of claim 1 wherein the at least one component is the frequency-based component, and wherein said comparing includes:

determining whether the frequency component in the tool motion is above the predetermined frequency component indicative of contact.

11. The method of claim 1 further comprising:

projecting a representation of the tool having a distal tip on an image; and indicating in a manner perceivable to the user that the tool has contacted the wall.

12. A system for detecting when a catheter contacts a wall of a heart cavity in a body, comprising:

a medical positioning system configured to determine a catheter position of the catheter with the body wherein the catheter includes a positioning sensor at a distal end thereof configured to sense one or more characteristics of a magnetic field produced by the medical positioning system and generate in response thereto a signal indicative of a sensor position of the positioning sensor, the medical positioning system being responsive to said signal to produce the catheter position;

a main control unit configured to (i) track the motion of said catheter and create a catheter motion profile; (ii) calculate a correlation value representative of a correlation between said catheter motion profile and a wall motion profile indicative of the motion of said wall, wherein calculating the correlation value comprises comparing at least one of the (1) frequency-based components, (2) time-based components and (3) spatial-based components of the tool motion profile with the corresponding at least one components of the wall motion profile, wherein the at least one component is the frequency-based component, and wherein said comparing includes determining whether a predetermined frequency component present in the wall motion is present in the tool motion; (iii) determine when said correlation value exceeds a threshold and producing an output indicating catheter-to-wall contact, said correlation value exceeding said threshold being indicative of contact of said catheter with said wall; and a contact indicator for signaling when the threshold level has been exceeded, therein indicating the tool is in contact with the wall of the region of interest.

13. The system of claim 12 wherein said medical positioning system is configured to generate time-based position data representative of said motion of said catheter comprising a plurality of catheter positions at respective times, said control unit being further configured to create said tool motion profile further as a function of said time-based position data.

14. The system of claim 12 wherein said control unit is further configured to create said wall motion profile based on wall motion data obtained from a motion measurement strategy selected from the group comprising image analysis, electrical parameter measurement including electro-cardiogram analysis, and positioning sensor-based measurements.

15. A system for detecting when a tool contacts a wall of a region of interest, the system comprising:
- a tool having a positioning sensor associated with the distal end of the tool for tracking the movement of the tool;
- a medical positioning system for determining a tool position of the tool within a body, said medical positioning system being configured to produce a magnetic field, said positioning sensor being configured to sensor one or more characteristics of said magnetic field produced by the medical positioning system and generate in response thereto a signal indicative of a sensor position of the positioning sensor, said medical positioning sensor being responsive to said signal to produce the tool position;
- a main control unit configured to
  (i) create a tool motion profile based on tracking the motion of the tool;
  (ii) calculating a correlation value representative of the correlation between the tool motion profile and a wall motion profile indicative of the motion of the wall, wherein calculating the correlation value comprises comparing at least one of the (1) frequency-based components, (2) time-based components and (3) spatial-based components of the tool motion profile with the corresponding at least one components of the wall motion profile, wherein the at least one component is the frequency-based component, and wherein said comparing includes determining whether a predetermined frequency component present in the wall motion is present in the tool motion; and
  (iii) determining when the correlation value exceeds a threshold, said correlation value exceeding said threshold being indicative of contact of the tool with the wall of the region of interest; and
- a contact indicator for signaling when the threshold level has been exceeded, therein indicating the tool is in contact with the wall of the region of interest.

16. The system of claim 15 further comprising
an imaging system for capturing an image of the region of interest; and
a display for displaying the point of contact of the tool with the wall on the image of the region of interest.

17. The system of claim 15 further comprising a reference tool having an region of interest sensor associated with the tool for evaluating the motion of the region of interest.

* * * * *